US00PP35070P2

(12) United States Plant Patent
Lee

(10) Patent No.: US PP35,070 P2
(45) Date of Patent: Mar. 28, 2023

(54) ***CLIFTONIA* PLANT NAMED 'BLCM03'**

(50) Latin Name: *BLCM03*
Varietal Denomination: Cliftonia monophylla

(71) Applicant: Robert Edward Lee, Independence, LA (US)

(72) Inventor: Robert Edward Lee, Independence, LA (US)

(73) Assignee: Plant Developent Services Inc., Loxley, AL (US)

( * ) Notice: Subject to any disclaimer, the term of this patent is extended or adjusted under 35 U.S.C. 154(b) by 0 days.

(21) Appl. No.: 17/892,317

(22) Filed: Aug. 22, 2022

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinctive *Cliftonia monophylla* plant, characterized by its unique pink flowers. Plants are globular and compact, reaching a mature height around 3 to 4 feet. Flowers are highly aromatic and attract a variety of pollinators. The new plant is a *Cliftonia*, typically useful as a landscape plant.

2 Drawing Sheets

Latin name of the genus and species: *Cliftonia monophylla.*

Variety denomination: 'BLCM03'.

BACKGROUND OF THE INVENTION

The present invention relates to a new and distinct variety of *Cliftonia monophylla*, which has been named 'BLCM03'. *Cliftonia monophylla* is an evergreen flowering perennial shrub that is used as an ornamental plant in landscape and novelty horticulture.

The new variety resulted from an open-pollination breeding program including unnamed, unpatented pink-flowering varieties of *Cliftonia monophylla*. The open-pollination occurred during the Fall of 2009 at a commercial nursery in Independence, La. The cultivar 'BLCM03' was selected in March of 2014 in a group of seedlings resulting from an open pollination of *Cliftonia monophylla* parents at the same nursery in Independence, La.

The new variety 'BLCM03' was first asexually propagated by vegetative stem cuttings at a nursery in Independence, La. during the Summer of 2014. Subsequent propagation has shown the features of the new variety are stable and reproduced true to type.

SUMMARY OF THE INVENTION

The cultivar 'BLCM03' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BLCM03'. These characteristics in combination distinguish 'BLCM03' as a new and distinct *Cliftonia* cultivar:

1. Unique pink flowers.
2. Easy to maintain in the landscape, maintaining a height of about 3 feet and a spread of about 4 feet with very little pruning.
3. Highly aromatic blooms, attractive to many pollinators.
4. Globular plant habit.
5. Hardy through zone 7.

PARENT COMPARISON

The parent varieties are unidentified.

COMMERCIAL COMPARISON

'BLCM03' can be compared to the *Cliftonia* variety 'Chipolo Pink', unpatented. Plants of the new cultivar 'BLCM03' are similar to plants of 'Chipolo Pink' in that both varieties produce pink flowers. However, plants of the new cultivar 'BLCM03' differ in the following:

1. This comparator is a small tree, growing to approximately 12 to 18 feet tall; the new variety is a compact shrub with a typical height around 3 feet.

'BLCM03' can also be compared to the *Cliftonia* variety 'BLCM05', filed concurrently. Plants of the new cultivar 'BLCM03' are similar to plants of 'BLCM05'in most horticultural characteristics, however, plants of the new cultivar 'BLCM03' differ in the following:

1. Plants of this comparator achieve a larger mature height by almost double.
2. Plant habit of this comparator is upright, plant habit of 'BLCM03' is rounded.
3. Plants of 'BLCM03' are denser than plants of 'BLCM05'.

BRIEF DESCRIPTION OF THE PHOTOGRAPHS

Figure 1:
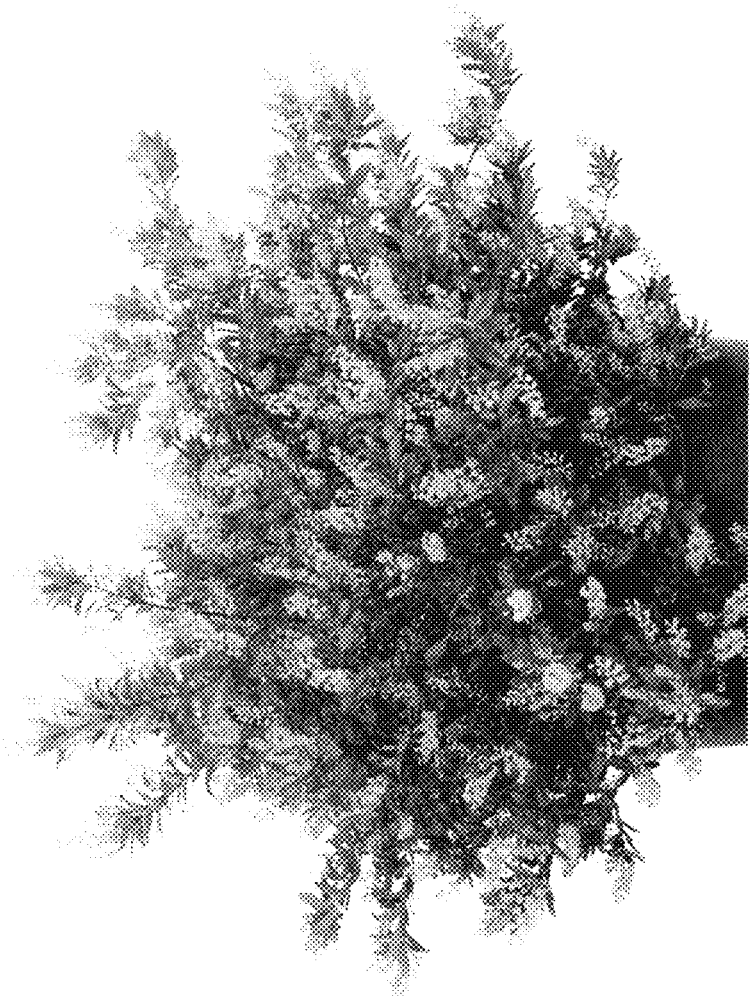

The accompanying photograph in FIG. 1 illustrates a typical plant of 'BLCM03' growing in a 3-gallon pot. The plant was grown outdoors in Loxley, Ala.

Figure 2:
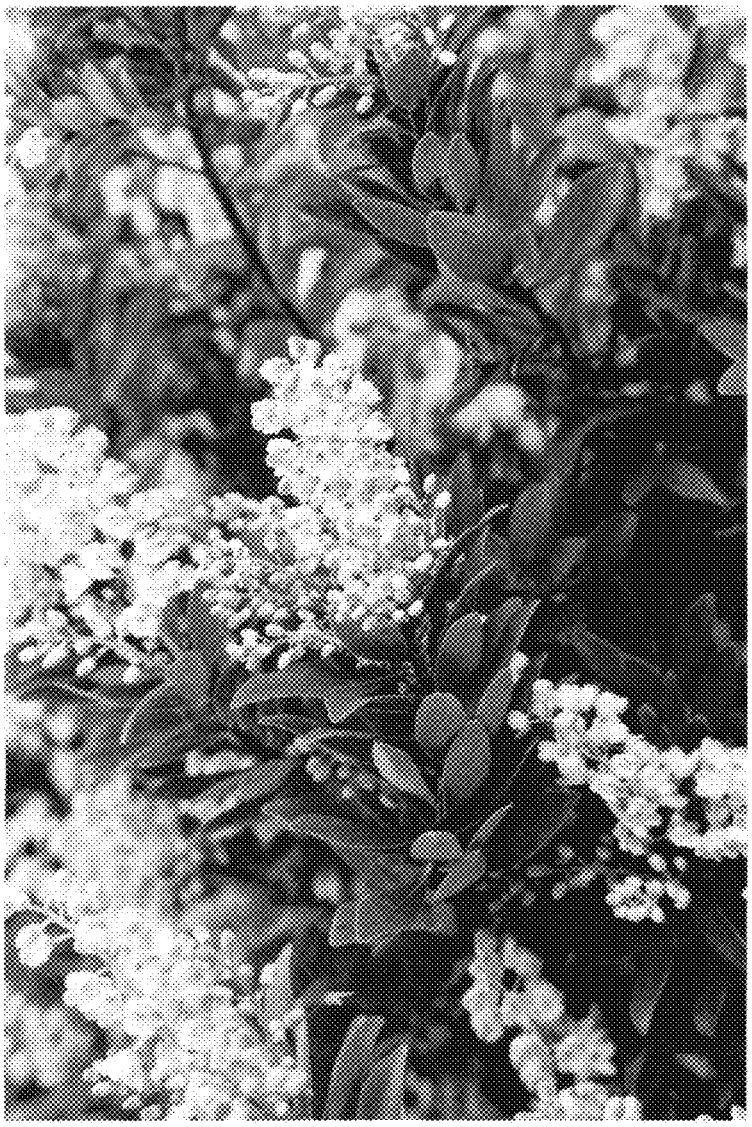

FIG. 2 illustrates in full color a close up of typical inflorescences of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BLCM03' plants grown outdoors in Loxley, Ala. Plants are approximately 2 years old, in a 3 gallon nursery container. Measurements and numerical values represent averages of typical plant types.

Botanical classification: *Cliftonia monophylla* 'BLCM03'.

PROPAGATION

Propagation method: Typically by stem cuttings in Summer.

Root description: Fine, fibrous young roots, well branched. Colored near RHS Grey-Brown 199A.

PLANT

Growth habit: Compact, globular shrub.

Height: Approximately 35 cm.

Plant spread: Approximately 45 cm.

Branching characteristics: 4 main basal branches, each splitting into 4 main lateral branches.

Primary branches:

Length of primary branches: Average 8 to 15 cm.

Diameter of primary branches: Average range 4 to 7 mm.

Primary branch strength: Very strong, difficult to break.

Primary branch color: Mature branches near Grey 201A. Immature branches near Greyed-Purple 183A.

Primary branch texture: Immature growth glabrous. Older growth scaly.

Lateral branches:

Length of lateral branches: Average range 5 to 10 cm.

Diameter of lateral branches: Average 3 mm.

Lateral branch strength: Strong.

Lateral branch color: Mature branches near Grey 201A. Immature branches near Greyed-Purple 183A.

Lateral branch texture: Immature growth glabrous. Older growth scaly.

Internode length: Average 2.0 cm to 3.5 cm.

Age of plant described: Approximately 2 years.

FOLIAGE

Leaf:

*Type.*—Simple.

*Arrangement.*—Whorled towards branches ends, foliage on lower portion of branches sub-opposite.

*Average length.*—Approximately 3.0 cm.

*Average width.*—Approximately 10 mm.

*Shape of blade.*—Elliptic.

*Apex.*—Acute.

*Base.*—Attenuate.

*Attachment.*—Sessile.

*Margin.*—Entire.

*Texture of top surface.*—Glabrous.

*Texture of bottom surface.*—Glabrous.

*Color.*—Young foliage upper side: Near RHS Green 137B. Young foliage under side: Near RHS Green 137B. Mature foliage upper side: Near RHS Green 139A. Mature foliage under side: Near RHS Green 138A.

*Venation.*—Type: Pinnate. Venation color upper side: Near RHS Yellow-Green 144B. Venation color under side: Near RHS Green 138B.

FLOWER

Bloom period: Early Spring until late Spring, early Summer.

Inflorescence: Elongated, slightly weeping raceme.

Raceme:

*Length.*—Average 5 to 8 cm. Excluding peduncle.

*Diameter.*—Average 2.0 cm.

Raceme peduncle:

*Length.*—Average 1.5 cm.

*Diameter.*—2 to 3 mm.

*Color.*—Near RHS Yellow-Green N144D.

*Texture.*—Glabrous.

*Aspect.*—Slightly arched.

Raceme pedicel:

*Length.*—Average 5 mm.

*Diameter.*—1 to 2 mm.

*Color.*—Near RHS Yellow-Green 145D.

*Texture.*—Glabrous.

*Aspect.*—Straight. Angle of attachment approximately 45° angle from peduncle.

Flowers:

*Quantity.*—Average 15 to 20 per raceme.

*Length.*—Average 5 mm.

*Diameter.*—Average 5 to 6 mm.

*Facing direction.*—Outwardly facing.

*Fragrance.*—None detected.

Petals:

*Petal number.*—6.

*Arrangement.*—Radial, slightly overlapping.

*Length.*—Approximately 3 to 4 mm.

*Aspect.*—Moderately upwardly cupped.

*Width.*—Approximately 3 mm.

*Apex.*—Acute.

*Base.*—Broad attenuate.

*Shape.*—Broad elliptic to obovate.

*Petal margin.*—Entire.

*Petal texture.*—Smooth, all surfaces.

*Color.*—Upper surface at first opening: Near RHS Greyed-Red 178C, large basal section near Red 49C. Under surface at first opening: Near RHS Greyed-Red 178C, large basal section near Red 49C. Upper surface at maturity: Near RHS Red-Purple 65D. Under surface at maturity: Near RHS Red 56A. Upper surface at fading: Near RHS Red-Purple 65D. Under surface at fading: Near RHS Red-Purple 65D.

Bud:

*Shape.*—Globular.

*Length.*—2 mm.

*Diameter.*—2 mm.

*Color.*—Near RHS Orange-Red N34C.

Calyx/sepals: Not present.

REPRODUCTIVE ORGANS

Stamens:

*Number.*—Approximately 9.

*Length.*—3 to 4 mm.

*Width.*—1 mm.
*Color.*—Near RHS Red 49D.

Anthers:
*Length.*—Approximately 1 mm.
*Color.*—Near RHS Greyed-Red 182A.
*Pollen.*—Scant, colored near RHS Red 37C.

Pistil:
*Number.*—1.
*Length.*—3 to 4 mm.
*Style.*—Highly reduced, less than 1 mm.
*Stigma.*—3 lobed, colored near Yellow-Green 144B, about 2 mm to 3 mm long.
*Ovary.*—Round approximately 1 mm in diameter. Colored near RHS Yellow-Green 144C.

OTHER CHARACTERISTICS

Disease and pest resistance: Not observed to be susceptible nor resistant to normal diseases and pests of *Cliftonia.*
Temperature tolerance: USDA Zones 7-10.
Drought tolerance: No tolerance for drought observed.
Fruit/seed production: Not observed to date.

What is claimed is:

1. A new and distinct cultivar of *Cliftonia monophyla* plant named 'BLCM03', substantially as described and illustrated herein.

* * * * *